United States Patent [19]

Inbar et al.

[11] Patent Number: 4,913,156
[45] Date of Patent: Apr. 3, 1990

[54] LITHOTRIPSY SYSTEM HAVING AN ULTRASONIC CALCULI LOCATOR

[75] Inventors: Dan Inbar, Haifa; Daniel I. Barnea, Tel Aviv; Abraham Bruck, Haifa, all of Israel

[73] Assignee: Elscint Ltd., Haifa, Israel

[21] Appl. No.: 403,067

[22] Filed: Sep. 5, 1989

Related U.S. Application Data

[63] Continuation of Ser. No. 268,621, Nov. 2, 1988, abandoned, which is a continuation of Ser. No. 737,532, May 24, 1985, abandoned.

[51] Int. Cl.⁴ .................. A61B 17/22; A61B 8/00
[52] U.S. Cl. .................. 128/660.03; 128/24 A
[58] Field of Search ............. 128/660.03, 24 A, 328

[56] References Cited

U.S. PATENT DOCUMENTS

| | | | |
|---|---|---|---|
| 3,237,623 | 3/1966 | Gordon | 128/24 A |
| 3,735,755 | 5/1973 | Eggleton et al. | 128/24 A |
| 4,315,514 | 2/1982 | Drewes et al. | 128/660 |
| 4,317,369 | 3/1982 | Johnson | 73/607 |
| 4,395,909 | 8/1983 | Steinberg et al. | 128/660 |
| 4,471,785 | 9/1984 | Wilson et al. | 128/660 |
| 4,526,168 | 7/1985 | Hassler et al. | 128/328 |
| 4,539,989 | 9/1985 | Forssmann et al. | 128/328 |
| 4,610,249 | 9/1986 | Makofski et al. | 128/328 |

FOREIGN PATENT DOCUMENTS

| | | | |
|---|---|---|---|
| 3127146 | 1/1983 | Fed. Rep. of Germany | 128/660 |
| 3320998 | 12/1984 | Fed. Rep. of Germany | 128/328 |

OTHER PUBLICATIONS

Chaussey et al., "Extracorporeal Shock Wave Lithotripsy", 1982.
Pan et al., "Tomographic Reconstruction of Ultrasonic Attenuation with Correction for Refractive Errors", IBM J. Res. Develop., vol. 25, No. 1, Jan. 1981, pp. 71–82.

*Primary Examiner*—Ruth S. Smith
*Attorney, Agent, or Firm*—Sandler, Greenblum & Bernstein

[57] ABSTRACT

A calculi locator is provided using an ultrasound transducer in combination with shock wave generator. Various means are provided for assuring coincidence of ultrasound obtained images of the calculi, the actual location of the calculi and of the target focal point of the shock wave generator means.

7 Claims, 5 Drawing Sheets

LITHOTRIPSY SYSTEM HAVING AN ULTRASONIC CALCULI LOCATOR

This application is a continuation of application Ser. No. 268,621, now abandoned which is a continuation of application Ser. No. 737,532 filed May 24, 1985 now abandoned.

FIELD OF THE INVENTION

This invention is concerned with extra-corporeal fragmentation of renal calculi, and more particularly with imaging systems used for locating calculi for use in cooperation with shock wave generators such as are used in lithotripsy procedures.

BACKGROUND OF THE INVENTION

One of the many ailments of mankind is the formation of calculi, that is stones or concrements, within the body. More common places for the development of such concrements are in the renal system and the gall-bladder. Some of these stones pass through the renal system without causing any adverse affects noticed by the person having the stones. Other stones lodge within the kidney, the bladders or passageways between kidney, the bladder and the exterior of the body causing pain or impairing the operation of organs; then the removal of the calculi becomes imperative.

Originally the only way of removing these stones was through invasive surgery. With the advent of improved imaging techniques it became possible to utilize percutaneous techniques for the removal of many of the calculi. The percutaneous techniques are also invasive and require the insertion of means such as a nephrotomy catheter to accomplish the stone removal. The catheters are equipped with devices to grasp the calculi or ultrasonic generators for fragmenting the calculi by vibrating while contigious thereto.

More recently, extra corporeal shock wave lithotripsy has been applied to fragment and thereby eliminate renal calculi.

A lithotripsy system now being used has a pair of substantially orthogonally positioned X-ray generators designed to exactly locate the stone to be eliminated. The patient is moved three-dimensionally in a bath so that cross-hairs on each of two images displayed by the system are juxtaposed to the stone. The cross-hairs are each at a line projection of the focal point of the shock wave generator. The patient is manipulated until the cross-hairs are superimposed on the image of the stone; at that time the shock wave generator is triggered and the shock waves focused to shatter the stone down to sizes where the fragments will be washed out of the body through normal body functions.

The imaging systems used presently for the calculi locating function leave room for improvement. Among other things it is desirable to reduce the exposure of the patient to X-rays. The patient presently is exposed to X-rays, originally to ascertain that stones are indeed causing problems and that they can be eliminated by lithotripsy. X-rays are used to align the stone with the focal point of the shock wave generator and X-rays are used subsequent to the application of the shock waves to assure that the stones have been shattered into fragments which can be disposed of by normal functions of the body. Thus, the procedure requires a relatively large dose of X-rays. It would be advantageous to lower the amount of X-ray radiation required in the lithotripsy process. To this end ultrasound has been tried in the past, but it did not prove successful. Additionally ultrasound radiation is more capable of imaging gallbladder stones than X-ray radiation.

In the prior attempts at using ultrasound as the medium for locating the calculi, different acoustic windows were used by the ultrasound transducers and by the shock wave generator without any correction being provided for the distortions of the ultrasound signals and the shock waves due to refraction, and/or the differences of the transmission velocities of the ultrasound signals and the shock waves in the different media traversed by those signals.

In addition in the past no provisions were made for enabling single transducers to image a plurality of planes for assuring accurate location of the calculi.

Similarily no provisions were made for varying the field of view of the individual transducers to provide for the different views required when searching for calculi and when centering the discovered calculi at the crosshairs.

Accordingly it is an object of the present invention to overcome the shortcomings of the prior art ultrasound imaging systems used in calculi location and to thereby improve on the presently available calculi locating imaging systems used in cooperation with extra corporeal shock wave lithotripsy.

BRIEF DESCRIPTION OF THE INVENTION

Accordingly a calculi locator is provided for use in cooperation with shock wave generators having spark terminals at a source focal point of a reflector with a target focal point spaced apart therefrom, said locator comprising:
means for imaging the calculi within patients, said imaging means comprising:
ultrasound scanning means for locating said calculi to enable positioning the calculi substantially at the target focal point of the shock wave generators, and
means for overcoming positioning errors caused by velocity differences in the various media traversed by the ultrasound signals in locating the calculi and by the velocity differences in the various media traversed by the shock wave when fragmenting the calculi.

A feature of the invention includes using ultrasound signal transducer means for imaging and combining the ultrasound transducer means with the shock wave generator means in a single movable probe with the focal points of the ultrasound transducer means and the shock wave generator means coinciding.

Another feature of the invention comprises providing substantially the same acoustic window for the shock waves and for the ultrasound signals to eliminate the need to correct for position errors caused by the different velocities in the different media traversed by both the signal and the wave between the probe and the calculi.

An alternative or related feature of the invention comprises means for computing and correcting the positioning errors caused by the signal velocity differences and by shock wave velocity differences.

Still another feature of the invention comprises providing means for rotating the ultrasound transducer means about its own axis to enable scanning in a plurality of planes and to enable more accurate positioning of the calculi at cross-hairs on the image indicating the target focal point.

A related feature of the invention comprises means for rotating said ultrasound transducer about the axis of the shock wave generator to provide various views of the patient and the calculi, while maintaining the coincidence of the target focal point and the transducer image cross-hair. The locations of the calculi obtained with the transducer in different positions are averaged to correct for positioning errors.

Another feature of the invention is the ability to image gallstones without the necessity of using dyes or the like.

Still a further feature of the invention comprises utilization of a pair of ultrasound transducers to speed the calculi locating process. The pair of ultrasonic transducers are arranged so that the cross-hair of each of the transducers is the target focal point of the shock wave generator with the planes imaged by the transducers being orthogonal or at least at angles to each other. Locating with each of the transducers individually enables a system computer to average the location to thereby overcome positioning errors without the necessity of rotating the single transducer about the shock wave generator.

Yet another feature of the invention comprises the use of a transducer with a long depth of field for general localization, and use of a sharply focused, short depth of field, transducer for accurate positioning of the calculi at the focal point.

A related feature is the use of single transducers providing both types of fields for use with the lithotripsy equipment.

Yet another feature of the invention includes using both x-ray and ultrasound along with the shock wave generator. The hybrid system is capable of image that would normally escape detection by the X-rays or the ultrasound alone.

BRIEF DESCRIPTION OF THE DRAWINGS

The above named and other features and objects of the present invention will be best understood when considered in the light of the following description of selected embodiments of the invention taken in conjunction with the following drawings; wherein.

GENERAL DESCRIPTION

Figure 1:
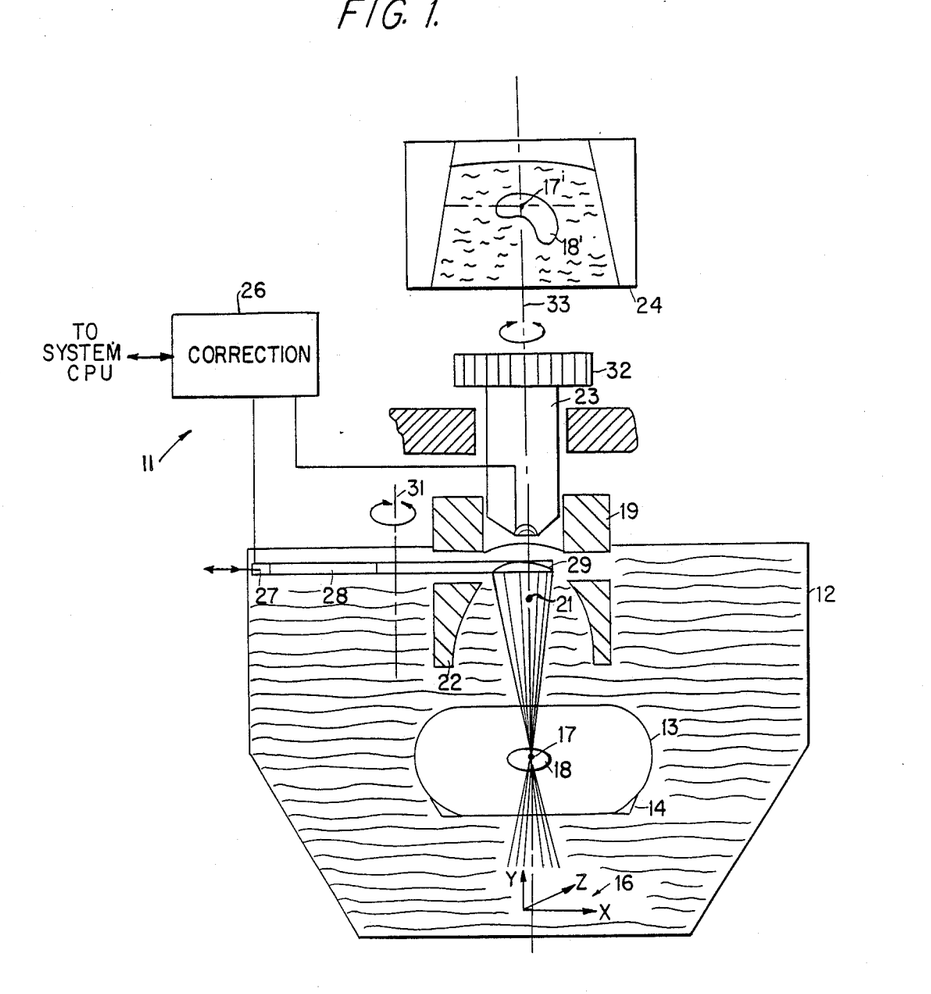
FIG. 1 is a cross sectional view of a broad aspect of an ultrasound calculi locator showing the transducer and shock wave generator using the same acoustic window.

In the illustration of FIG. 1 an overall extra-corporeal calculi fragmenting system 11 is indicated in cross sectional and block diagram form. The indicated system comprises a bath 12 in which the patient 13 is partially submerged during the treatment. A hydraulic or mechanical system for supporting and moving the patient in the X, Y and Z directions is indicated by a bed 14 and the axes of movement XYZ shown generally at 16. The patient 13 is shown with a stone 17 located in a body organ such as a bladder, kidney or gallbladder indicated generally at 18.

A shock wave generator 19 is provided. The shock wave generator has a pair of spark terminals, for example, indicated at 21. The location of the terminals is at a source focal point in a partial ellipsoid 22. The target focal point of the shock waves generated at the source focal point and reflected by the walls of the ellipsoid is at the location of the stone 17. The patient 13 is moved until the stone is at the target focal point location by movement of the support 14. The stone is shown within the body organ 18.

It should be understood that while spark terminals are shown in a partial ellipsoid the principal idea is that shock waves are generated by any means and focused by any suitable reflector at a target focal point so that the stone 17 may be set at the target focal point.

Means are provided for imaging the calculi, more particularly ultrasound transducer 23 is provided. The transducer in one embodiment is a sector scanning type of focused transducer and its focal point coincides with the target focal point of the shock wave generator 19 at some time during the scan. The echoes received from the stone and from the body in general are processed in the normal manner of processing ultrasonic echo signals to provide an image shown on the display means 24. The image includes an image of the calculi shown as 17' located in the image 18' of the body organ.

Means are provided for correcting for the calculi location errors normally incurred with ultrasound waves due to refraction and differences in velocity of both the ultrasound signals and the shock waves when travelling through the different media between the transducer and the calculi. The unique means are either or both computational means indicated at block 26 or positioning means for positioning the ultrasound transducer to have the same acoustic window as the shock wave generated by the shock wave generator 19. The computation means can either entail actual computations based on data obtained by the echo signals and/or based on data stored in the computer used with the imaging system In the showing of FIG. 1 the transducer positioning means for overcoming calculi location errors is abetted by a moving member 27. The moving member includes an aperture 28 and an ellipsoidal section 29. The alternate placement of an ellipsoidal section or an aperture can be achieved by many means, such as by rotation of the moving member or by a sliding or reciprocating movement of the member in a linear direction.

Thus, the member 27 can rotate about the axis 31 or reciprocate to alternately provide an ellipsoidal section that attaches to the partial ellipsoid 22. The ellipsoidal section assures that the shock waves generated by spark gap terminals 21 have available more reflecting mirror surfaces. Alternatively, the aperture 28 enables the ultrasonic signals to be transmitted and the echoes to be received. The correction means 26 indicated herein controls and times the rotation or reciprocation of member 27. In this manner both the ultrasonic waves and the shock waves have substantially the same acoustic window to the patient 13. Thus, if there is any refraction acting on the ultrasonic waves, almost the same refraction acts on the shock waves, and any positioning error due to the refraction of the ultrasonic signals is cancelled out by the positioning error of the shock waves.

Means are provided for rotating the ultrasound transducer about its own axis which coincides with the line of sight between the transducer and the target focal point to enable imaging more than one plane. The means is generally shown in FIG. 1 by the gear 32, the gear as indicated is used to rotate the transducer about its own axis 33. The ability to rotate the transducer can be used to improve the ability to correctly position the calculi and to ascertain that the calculi is indeed in the correct position. When the calculi has indeed been correctly positioned then the rotation of the transducer will not affect the position of the cross-hair on the image of the stone.

Figure 1A:
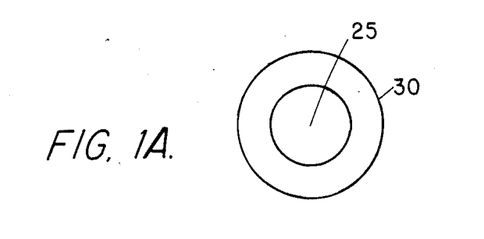
FIG. 1A shows a front view of a particular transducer for use in the ultrasound calculi locator of FIG. 1.

FIG. 1A shows the front view of a single transducer 23 that enables the two modes of operations useful in cooperation with lithotripsy equipment, i.e. (1) searching and (2) accurately positioning. One mode (the smaller diameter dish 25) provides a transducer having a relatively long depth of field and medium focusing for localization of the effected organ and the calculi therein. The other mode (the larger diameter dish 30) provides a transducer having a sharp focus and a short depth of field for accurate positioning of the calculi at the target focal point.

The transducer is shown as being circular. Preferably it is a piezoelectric crystal type transducer focused at about 200 mm having two active areas—an internal circular area 25 (in a preferred embodiment a 30 mm dish) surrounded by an annulus 30. For searching (the search mode) only the internal area is used. For positioning the combinations of the internal area and the annulus are used in a preferred embodiment. The combination is a 50 mm dish. Alternatively two separate transducers may be used and the sharp focus can alternately be provided by a focused phased array transducer arrangement.

Figure 2:
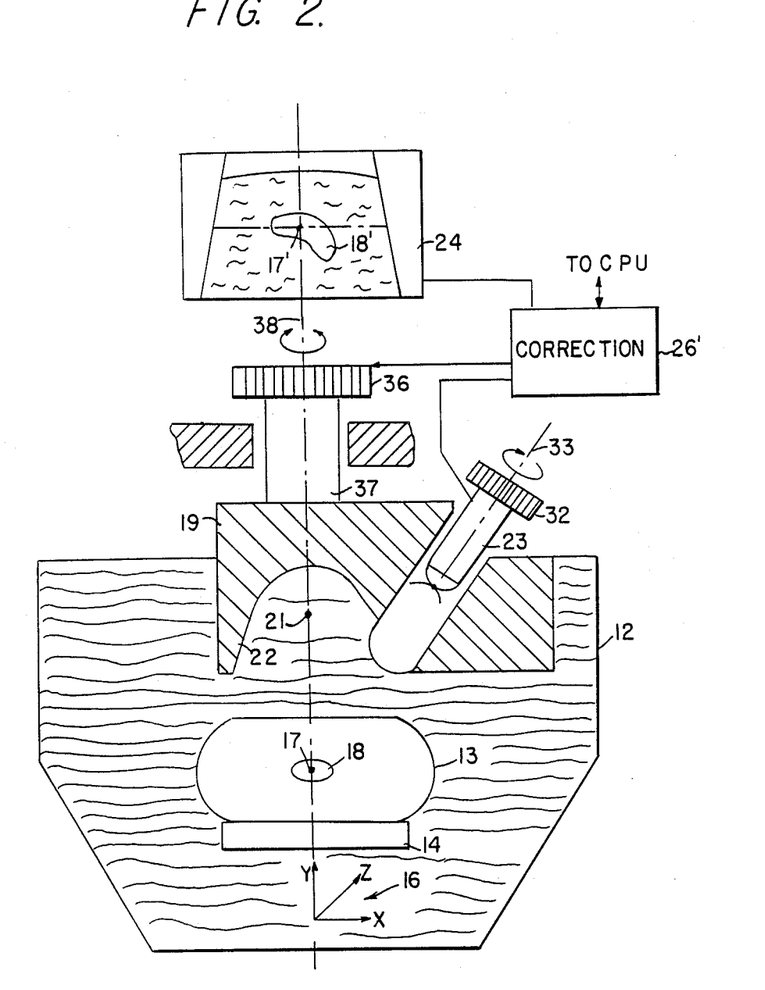
FIG. 2 is another sectional drawing of an ultrasound calculi locator, showing the ultrasonic transducer removed from the shock wave generator window.

In the embodiment of FIG. 2 the transducer 23 is shown removed from being at the exact window location of the shock waves generated by the spark terminals 21. The same number designations are used in FIG. 2 as were used in FIG. 1. A correction means 26', is indicated in FIG. 2 in place of correction means 26, because in FIG. 2 there is no movable member 27. Instead a numerical or computation correction is made to overcome the calculi location errors. The correction afforded by unit 26', will be explained in greater detail hereinafter.

Figure 3:
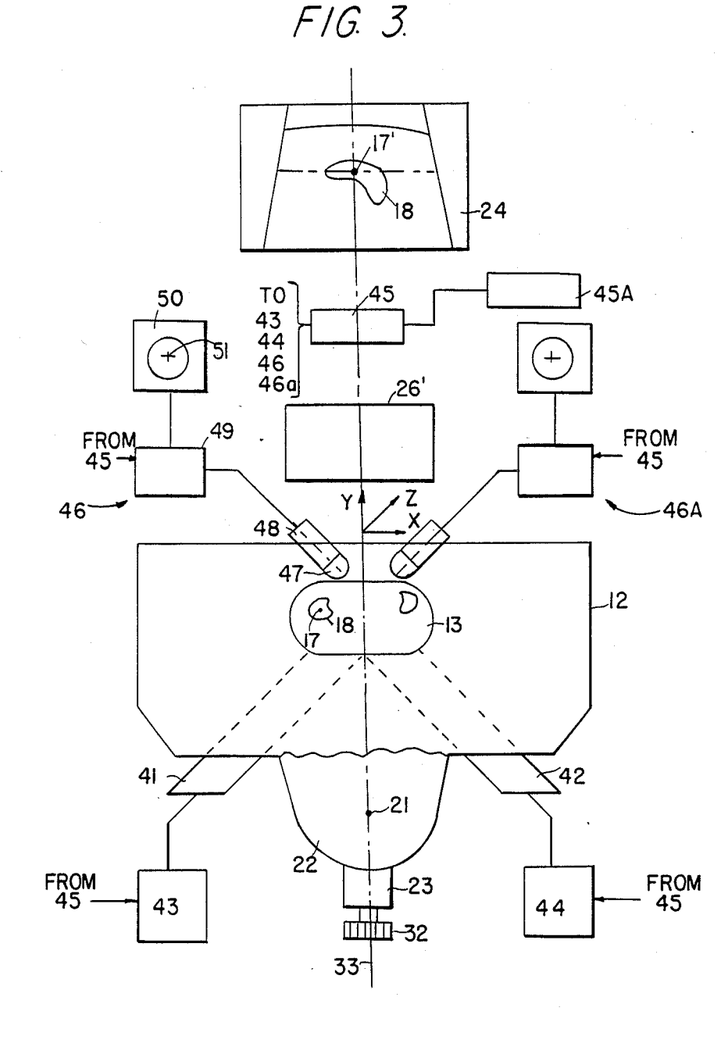
FIG. 3 is another cross sectional drawing of an embodiment of the ultrasound calculi locator showing the ultrasound transducer and shock wave generator positioned at the bottom of a lithotripsy bath along with X-ray tubes whereby a hybrid X-ray ultrasound calculi locator is provided.

An additional feature and another way of overcoming the calculi location errors is shown in FIG. 2 as the capability to rotate the transducer 23 about the axis 38 of the shock wave generator 19. More particularly means are provided for rotating the transducer about the longitudinal axis 38 of the ellipsoidal reflector of the shock wave generator 19. These means are indicated as the gear 36 shown at the top of column 37 fixedly attached to the shock wave generator 19. The shock wave generator rotates about the axis 38 responsive to and under control of the central control unit of the lithotripsy system. The rotation of the shock wave generator 19 causes the transducer 23 to rotate about the axis of rotation 38 but to maintain its focal point coincident with the focal point of the shock wave generator, i.e. maintain the cross-hairs on the calculi. Actual differences in the position of the imaged calculi are averaged to overcome or reduce calculi location errors FIGS. 1 and 2 show the shock generator and ultrasound transducer assembly mounted above the patient when the patient is located within the bath. However, the shock wave generator transducer assembly could just as easily be mounted at the bottom of the bath as illustrated in FIG. 3. It should be understood that while FIG. 3 shows the transducer using the same acoustic window as the shock wave generator the window of the transducer could be removed from that of the shock wave generator by utilizing computational corrections such as done in FIG. 2 with the exception that the assembly is mounted at the bottom of the bath.

It should be further understood of course with the system mounted at the bottom of the bath, greater care has to be taken during the rotation of either the transducer and/or the shock wave generator to prevent leakage. However, the steps necessary are well known to those skilled in the art. The numbers of FIG. 3 correspond to the numbers used in FIG. 2.

A feature of the invention includes the use of X-ray equipment in addition to the ultrasound equipment for locating the calculi. The hybrid system is capable of finding and triangulating calculi that could possibly escape detection when only one type of radiation is used. In addition the X-ray equipment is useful for overcoming the calculi location errors that may occur when using the ultrasound equipment. Thus, the X-ray equipment could be used as a vernier after the calculi is ranged by the ultrasound equipment.

The X-ray equipment includes a pair of X-ray tubes positioned to direct X-rays toward the target focal spot of the shock wave generator. The tubes 41 and 42 are positioned so that their rays are at an angle to each other and preferably the angle is a right angle. The tubes are shown powered by high voltage generators 43 and 44 under control of a central control unit 45.

Associated with each tube, on the opposite side of the patient 13 are data aquisition and imaging systems 46 and 46a. The data acquisition system 46 include detector means such as image intensifier 47 for converting the X-rays which have passed through the patient to position related light intensity signals.

Means such as video camera 48 is used to convert the position related light intensity signal to pixel related electrical signals. Video processor means 49 converts the pixel related electrical signals to the image displayed on monitor 50. A cross-hair 51 is shown on the monitor. The cross hair represents the line of sight projection of the target focal point as detected by system 46. System 46a is a duplication of the equipment of system 46. Both systems are under the control of unit 45. The hybrid system of FIG. 3 is equipped to locate the calculi, and position it at the target focal point using ultrasound, or X-rays or the combination of ultrasound and X-rays.

To minimize patient movement or movement of the organs triggering means 45a are provided. Triggering means causes the system to operate only during prescribed physical occurrences by triggering on a ECG signal, for example.

Figure 4:
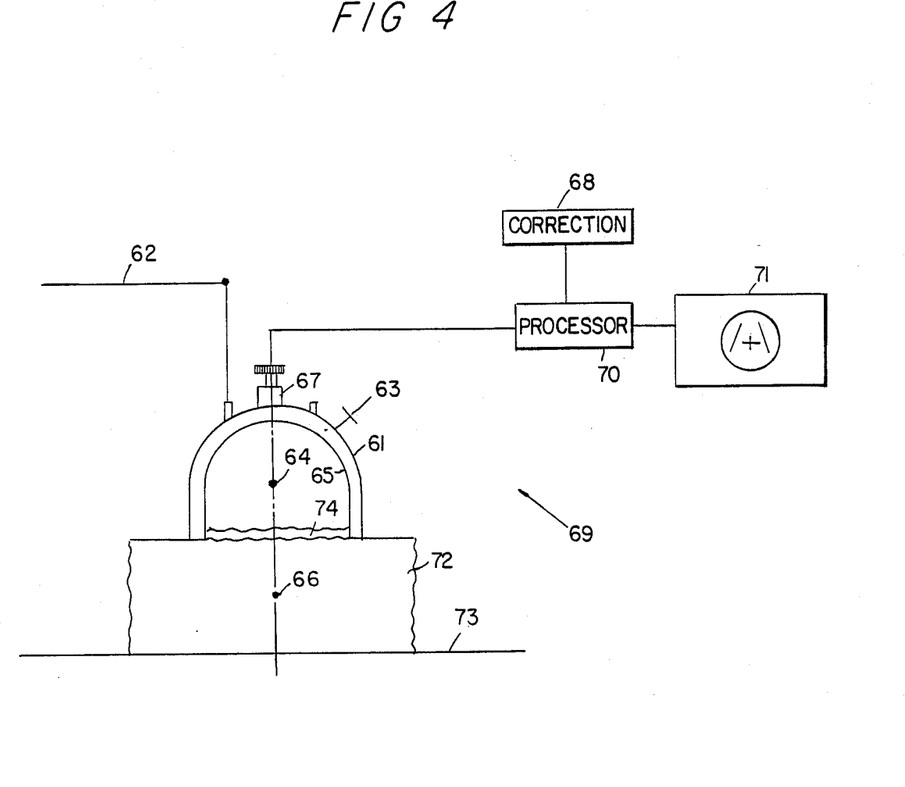
FIG. 4 is a cross section block diagram showing of an ultrasonic calculi locator combined in a movable shock wave generator wherein the combination comprises a probe whereby a bath is not necessarily required.

Means are provided for using an assembly of a shock wave generator and an ultrasound transducer in a movable probe. More particularly, a probe 61 in FIG. 4 is shown. The probe is shown mounted from and supported by a gantry indicated generally as 62. A handle 63 is used for moving the probe, the probe comprises the spark terminals 64 fixed at a shock wave source focal point in a reflecting and focusing mirror such as in an ellipsoidal mirror shown at 65. The ellipsoidal reflector has a second or target focal point 66 spaced apart from the source focal point 64 at a fixed location. An ultrasound transducer 67 is also focused at the target focal point 66. The ultrasound transducer is shown as having the same acoustic window as the shock wave generator; that is the transducer is mounted directly behind the spark gap terminals 64. In the illustration shown, a portion of the mirror is removed and replaced by the transducer scanning portion.

Alternatively the system of FIG. 1 could be used within the scope of this invention; that is an ellipsoidal portion and an aperture could alternately be placed in front of the transducer. Also alternatively the transducer could be mounted to the side and have a slightly different window than the shock wave generator. A location error correction unit 68 operates in conjunction with the echo of the ultrasonic system indicated generally at 69 to provide images for display means 71 under the control of processor 70.

A portion of the patient's body is shown at 72 lying on a support bed or support table 73. The system where the probe 61 comprise the assembly of the shock wave generator and transducer obviates a necessity of placing the patient in a water bath. Instead the assembly 61 has water in its interior and maintained within the probe by a diaphragm 74. Jellys are used between the patient 72 and the diaphragm 74 to aid in transferring the shock wave and ultrasonic signal with the least amount of resistance from the probe into the patient. Of course the probe could be used in a water bath.

Figure 5A:
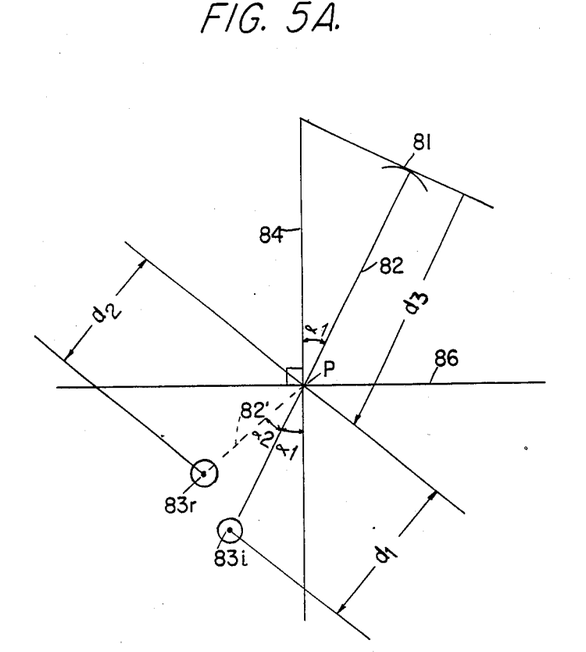
FIG. 5A is a line drawing to show positional errors caused by ultrasound signal velocity differences in the different media traversed by the signals.
Figure 5B:
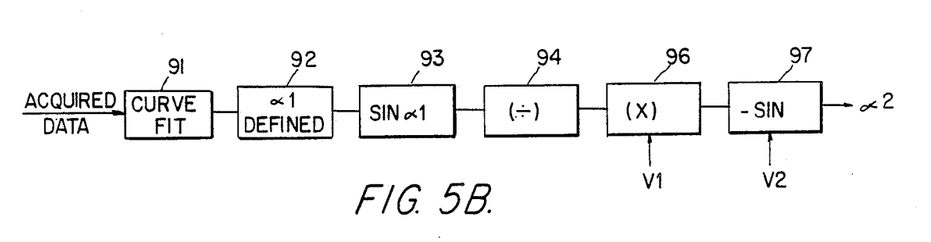
FIG. 5B is a block diagram showing positional error correction calculation means for use with the ultrasonic calculi locator.

FIG. 5 is used to explain the correction computations used to overcome the calculi location errors occurring because of the differences in the velocity of the ultrasonic signals in the different media traversed between the transducer and the calculi in the patient.

In FIG. 5A the ultrasound transducer 81 projects a series of beams as it scans over an arc. The beams are represented by the central beam 82. The beams cause echoes to be generated by tissue boundaries, for example. The calculi generates such an echo.

The system normally treats the beam and the echo as if they had travelled along a straight line. Actually because of the differences between the velocity of the sound waves in water and in tissue, the calculi 83 which really is at location 83r appears at location 83i. Thus, there is an angular error $\alpha 2 - \alpha 1$ and a distance error $d1 - d2$, where:

$\alpha 1$ is the angle between the beam 82 and the normal 84 to the skin surface 86 at point p, where the beam is incident to the skin surface, $\alpha 2$ is the angle between the refracted beam 82', and the normal to the skin surface at the point p, d1 is the distance from point p to the apparent position of 83i of the calculi, and d2 is the distance from the point p to the actual position 83r of the calculi.

The angles and the velocities are related by Snell's Law:

$$\sin\alpha 1 / \sin\alpha 2 = V1 / V2$$

where:

V1 is the velocity of sound in water, 1500 m/sec, and

V2 is the average velocity of sound in tissue, 1540 m/sec.

The distance d2 is easily determined. The time t1 for the echo to return from the calculi is known. That time multiplied by the velocity of sound in the tissue gives the distance to the calculi along beam 82', Normally the distance between the source and the object using a single velocity results in an error along the direction of the vector as well as an angular deviation due to Snell's law. During the first few frames the ultrasonic system will detect the position 86 of the skin surface. The position of the skin surface stands out because, as is well known, it is the first strong echo received.

FIG. 5B shows an embodiment of equipment for calculating the angle between the ultrasound beam and the normal to the skin surface for every imaging vector. A curve is fit to the data obtained to indicates the skin surface 86. Thus FIG. 5B shows a curve fitting means 91. The curve fitting means could be any well known means for curve fitting, such as a mean square operator using the data obtained at the skin. After a curve is fitted, the angle $\alpha 1$ between the normal to the skin and the beams going from the transducer to the patient is obtained in means 92. The angle is obtained for each of the beams incident to the skin. The sin of the angle $\alpha 1$ is calculated at 93 and divided by the value V1 at 94. The quotient is multiplied by V2 at 96 which gives a value of sin $\alpha 2$. The angle $\alpha 2$ is obtained from this value at 97. The value of $\alpha 2$ enables finding the actual line (i.e. line 82',) for each of the beams upon which the real calculi is located.

Similar calculations may be made for also correcting the shock wave generator target focal point for positional errors due to velocity differences and refraction. The corrected transducer focal point is set to coincide with the corrected target focal point.

In practice the probe comprising the assembly of an ultrasonic transducer and a shock wave generator is used to determine the location of calculi and to destroy the calculi by the lithotripsy with shock waves generated extra corporeally. The actual location of the calculi is obtained either by: using the same window for the shock waves and for the ultrasound transducer, rotating the transducer about the axis of the shock wave generator and averaging calculi locations obtained, rotating one transducer about its own axis and averaging calculi locations, using two transducers and averaging calculi locations, or by calculating the real position from the data obtained during the use of the ultrasound transducer and X-ray equipment, or combinations of the above. The actual location is shown on the image and the patient or probe is moved until the cross hairs on the image coincide with the imaged calculi. At which time, the shock wave generator is triggered. After a series of shock waves have been generated and transmitted to fragment the calculi, the image is again provided to check to see if the calculi has indeed been fragmented and to further check and see if any of the fragments need further fragmentation.

While the invention has been described with regard to specific embodiments it should be understood that these embodiments are made by way of example only and not as a limitation on the scope of the invention, which is defined by the appended claims.

What is claimed is:

1. A calculi locator in combination with a spark gap shock wave generator for shattering calculi in body organs of a patient, said shock wave generator comprising:

spark gap terminals located at a source focal point in an ellipsoidal reflector for producing shock waves that are reflectively focused at a target focal point spaced apart from said spark gap terminals; said calculi locator comprising:

ultrasound transducer scanning means providing ultrasound transmitter signals and receiving echo signals, means for using said echo signals for obtaining an image location of calculi in a patient for use in positioning the calculi at the target focal point, means for positioning said ultrasound transducer scanning means outside of said ellipsoidal reflector along the longitudinal axis of the ellipsoidal reflector on the side of said spark gap terminals away from said patient so that shock waves produced by the shock wave generator and said ultrasound signals pass through the same acoustic window;

a portion of said ellipsoidal reflector that traverses the longitudinal axis and that is in front of said transducer scanning means being movable away from the front of said transducer scanning means;

aperture means being movable into the place of the movable portion of said ellipsoidal reflector in front of said transducer scanning means when said transducer scanning means is transmitting or receiving, ultrasound image means for assuring coincidence of the true location of the calculi and the image location to correctly place the calculi at the shock wave generator target focal point, and means for selectively placing said aperture means or said movable portion of the ellipsoidal reflector, respectively, in front of said transducer scanning means to minimize interference with said transmitting and receiving when the transducer scanning means is operative or to maximize shock waves received at the target focal point when said shock wave generator is operative.

2. The calculi locator of claim 1 wherein said means for selectively placing said aperture means or said portion of said ellipsoidal reflector surface in front of said transducer scanning means comprises rotating means.

3. The calculi locator of claim 1 wherein said means for selectively placing said aperture means or said portion of said ellipsoidal reflector surface in front of said transducer scanning means comprises sliding means.

4. The calculi locator of claim 1 including means for rotating said transducer scanning means about its longitudinal axis to enable acquiring images in a plurality of different planes with a single transducer.

5. The calculi locator of claim 1 wherein said transducer means comprise sector scanning transducer scanning means.

6. The calculi locator of claim 1 wherein said transducer means comprises focused phased array transducer scanning means.

7. The calculi locator of claim 1 wherein said transducer scanning means includes means for varying the depth of field to enable both searching and accurate positioning.

* * * * *